(12) United States Patent
Adams et al.

(10) Patent No.: US 10,932,907 B2
(45) Date of Patent: Mar. 2, 2021

(54) SEMI-FLEXIBLE ANNULOPLASTY RING (75) Inventors: David H. Adams, New York, NY (US); John T. M. Wright, Conifer, CO (US)

(73) Assignee: Medtronic, Inc., Minneapolis, MN (US)

( * ) Notice: Subject to any disclaimer, the term of this patent is extended or adjusted under 35 U.S.C. 154(b) by 891 days.

(21) Appl. No.: 13/576,982

(22) PCT Filed: Feb. 1, 2011

(86) PCT No.: PCT/US2011/023386
§ 371 (c)(1),
(2), (4) Date: Jan. 29, 2013

(87) PCT Pub. No.: WO2011/097251
PCT Pub. Date: Aug. 11, 2011

(65) Prior Publication Data
US 2013/0204361 A1    Aug. 8, 2013

Related U.S. Application Data (60) Provisional application No. 61/301,158, filed on Feb. 3, 2010, provisional application No. 61/301,532, filed on Feb. 4, 2010.

(51) Int. Cl.
*A61F 2/24* (2006.01)

(52) U.S. Cl.
CPC ........ *A61F 2/2445* (2013.01); *A61F 2/2466* (2013.01); *A61F 2250/0018* (2013.01)

(58) Field of Classification Search
CPC .... A61F 2/2442; A61F 2/2445; A61F 2/2448; A61F 2/2466; A61F 2250/0018
USPC .............................. 623/2.36, 2.37, 2.38, 2.41
See application file for complete search history.

(56) References Cited

U.S. PATENT DOCUMENTS

| | | | | |
|---|---|---|---|---|
| 4,055,861 A | * | 11/1977 | Carpentier et al. | 623/2.36 |
| 5,674,279 A | * | 10/1997 | Wright et al. | 623/2.37 |
| 5,824,066 A | * | 10/1998 | Gross | 623/2.36 |
| 6,187,040 B1 | * | 2/2001 | Wright | A61F 2/2448 |
| | | | | 623/2.36 |
| 2005/0182487 A1 | * | 8/2005 | McCarthy et al. | 623/2.11 |
| 2008/0086203 A1 | * | 4/2008 | Roberts | 623/2.36 |
| 2009/0036979 A1 | * | 2/2009 | Redmond et al. | 623/2.36 |

(Continued)

FOREIGN PATENT DOCUMENTS

| | | |
|---|---|---|
| WO | WO2010/078121 | 7/2010 |
| WO | WO2012/074993 | 6/2012 |

OTHER PUBLICATIONS

EP11740273.5, European Search Report, dated Oct. 29, 2015.

*Primary Examiner* — Jerrah Edwards
*Assistant Examiner* — Rokhaya Diop
(74) *Attorney, Agent, or Firm* — Dicke, Billig & Czaja, PLLC (57) ABSTRACT

An annuloplasty ring for attachment to an annulus of a tricuspid valve comprises an elongate tube of suturable material comprising a central segment and first and second end segments. An arcuate stiffener is received in the central segment of the tube and extends the length thereof. The arcuate stiffener is circumferentially confined within the central segment to prevent circumferential movement of the stiffener relative to the tube. The first and second end segments of the tube lack a stiffener and are axially deformable.

16 Claims, 9 Drawing Sheets

(56) References Cited

U.S. PATENT DOCUMENTS

2009/0088838 A1* 4/2009 Shaolian ............... A61F 2/2445
                                                        623/2.37
2009/0264996 A1* 10/2009 Vanermen ............ A61B 5/1076
                                                        623/2.36
2010/0168845 A1* 7/2010 Wright .................. A61F 2/2448
                                                        623/2.36

* cited by examiner

SEMI-FLEXIBLE ANNULOPLASTY RING

TECHNICAL FIELD

Annuloplasty rings for heart valve repair, and more particularly, a semi-flexible annuloplasty ring to treat functional tricuspid regurgitation.

BACKGROUND

The anatomy and physiology of the human heart is well known. Of the four one-way valves in the heart, the two inlet valves are the mitral valve of the left side of the heart, and the tricuspid valve on the right side of the heart. The tricuspid valve is located between the right atrium and the right ventricle. The three leaflets of the tricuspid valve laterally terminate at the tricuspid annulus. Blood flows from the superior and inferior vena cava into the right atrium, then through the tricuspid valve during diastole to fill the right ventricle. During ventricular systole, the tricuspid valve is closed and blood is ejected through the pulmonary valve into the pulmonary artery and hence through the lungs. At the end of ventricular systole the pulmonary valve closes. Leaving the lungs, the now oxygenated blood flows into the left atrium and hence through the mitral valve into the left ventricle during ventricular diastole. Finally, at ventricular systole the mitral valve closes and blood is ejected through the aortic valve into the aorta. However, should the mitral valve become regurgitant due to disease then some percentage of the left ventricular stroke volume will flow backwards through the mitral valve into the left atrium. This regurgitation causes the left atrial pressure to rise, in turn causing pulmonary artery pressure to rise, that is reflected back to the right ventricular pressure. This mechanism was more fully described by Shiran and Sagie (Shiran and Sagie (2009) J. Am. Coll. Cardiology 53:401-408, "Tricuspid Regurgitation in Mitral Valve Disease: Incidence, Prognostic Implications, Mechanism, and Management") the contents of which, along with contents of all references cited herein, are incorporated herein in their entirety.

Figure 1:
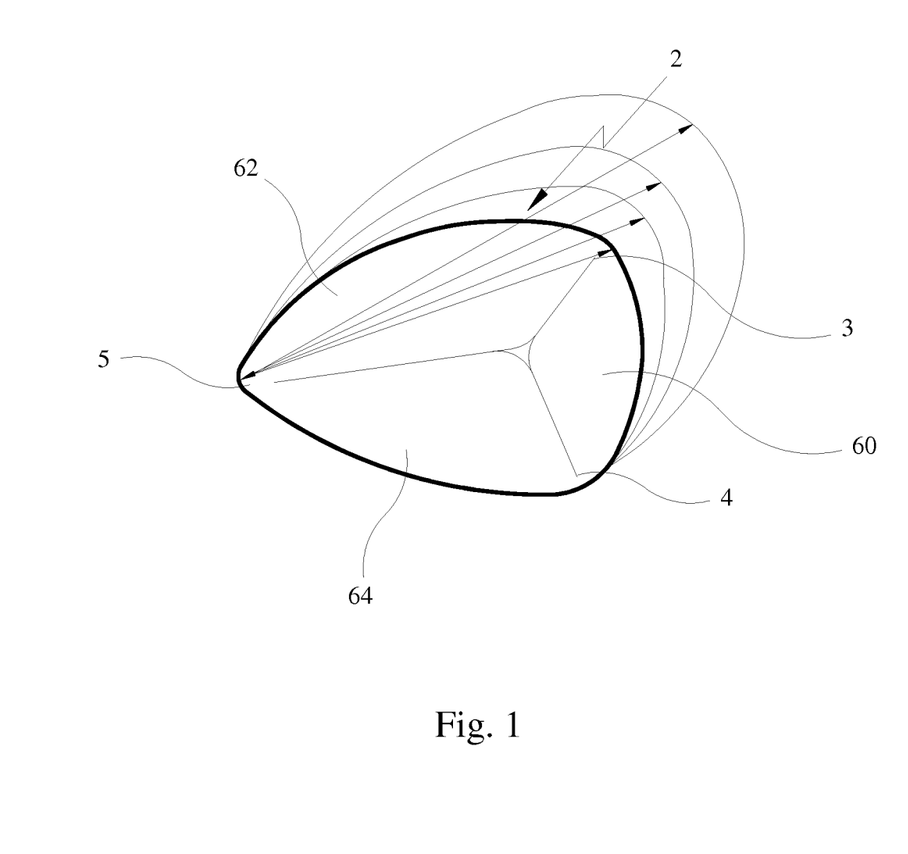
FIG. 1 is a schematic plan view of a tricuspid valve illustrating a normal tricuspid valve annulus and its progressive asymmetrical enlargement causing functional tricuspid regurgitation as depicted by Dreyfus.

The right ventricle is a thin walled muscular "pocket" wrapped around the main musculature of the left ventricle. Without being bound by theory, as a result of the above-described ventricular pressure, the thin-walled right ventricle and a portion of the tricuspid annulus may dilate. Initially, tricuspid leaflet coaptation is reduced, but the valve remains competent. Later, when the tricuspid annulus is further dilated leaflet coaptation is lost and tricuspid valve regurgitation results. This is known as functional tricuspid regurgitation because the tricuspid valve leaflets remain normal. The problem lies with the dilated annulus in the anterior and posterior segments. This was first described by Bex and LeCompte (Bex and LeCompte (1986) J. Cardiac Surgery 1:151-159, "Tricuspid Valve Repair Using a Flexible Linear Reducer") and later by Dreyfus (Dreyfus, et al. (2005) Ann Thoracic Surgery 79:127-32, "Secondary Tricuspid Regurgitation or Dilation: Which Should Be the Criteria for Surgical Repair?"). FIG. 1, which is adapted from Dreyfus, illustrates dilation of the tricuspid annulus 2, the relative position of the posterior leaflet 60, anterior leaflet 62 and septal leaflet 64 as well as the anterior/posterior (A/P) commissure 3, posterior/septal (P/S) commissure 4 and septal/anterior (S/A) commissure 5.

Deformation of the tricuspid annulus by other means than that described above might also lead to functional tricuspid valve regurgitation.

A significant surgical problem that exists today is the operative recognition of the severity of the tricuspid valve regurgitation problem. Immediately prior to mitral valve surgery the patient is anaesthetized and an esophageal ultrasonic probe is introduced and mitral and tricuspid regurgitation assessed. One difficulty is that one effect of the anesthesia may be to significantly suppress tricuspid regurgitation. The ultra-sonic probe display may lead a surgeon incorrectly to believe that the tricuspid regurgitation is absent or minimal. Unfortunately, later, post-operatively when the drugs have worn off, the true level of tricuspid regurgitation typically becomes much more severe than that indicated intra-operatively or pre-operatively. Regrettably, reoperation mortality on patients with tricuspid regurgitation is about 30%, but worse, if severe tricuspid regurgitation is left untreated, 5 year patient survival is only about 50%. This suggests that many more patients undergoing mitral valve repair should also have concomitant tricuspid annulus reduction than is currently the case. The current rate of tricuspid annuloplasty reduction associated with mitral valve repair varies between about 5% and 60%. At the high end of the range are surgeons at centers of excellence who operate early on patients with mitral valve disease before right ventricular and tricuspid dilatation becomes significant. But, many other surgeons fail to appreciate that the minor tricuspid regurgitation diagnosed pre-operatively or intra-operatively may later become severe, even as early as in the recovery room after the effects of the anesthetics have worn off.

Early repairs of the tricuspid valve annulus were described by De Vega (De Vega (1972) Rev Esp. Cardiol. 6:555-557, "La anuloplastia selective, regulable y permanente") who used a double continuous 2/0 or 3/0 polypropylene suture which ran along the anterior and posterior annulus, corresponding to the right ventricular free walls. A drawback of the technique was and remains a tendency for the sutures to tear out of the tissue. However, a modified De Vega technique described by Antunes (Antunes (2003) Operative Techniques in Thoracic and Cardiovascular Surgery De Vega 8:169-76, "De Vega annuloplasty of the tricuspid valve") using 11-13 pledgets, although adding complexity and time to the operation, appears to mitigate the dehiscence problem.

Other methods and devices have been used to treat functional tricuspid regurgitation including the use of flexible or, alternatively, rigid annuloplasty rings, each of which has demonstrated at least one problem. When implanting, tricuspid annuloplasty rings several precautions are needed, in particular the atrioventricular (AV) node must be avoided by the implantation suture, and in this regard the gap of known C-shaped annuloplasty rings may be too small and allow implantation suture to penetrate the AV node and cause heart block. Another issue when implanting a flexible ring on the tricuspid annulus is correct placement of the implant on the annulus. Yet another issue is that the tricuspid annulus is in a roughly concave plane rather than a flat plane. As functional tricuspid regurgitation advances the annulus becomes less concave and more flat. Thus, an entirely rigid tricuspid ring may not conform well to the annulus.

The present invention is directed toward overcoming one or more of the problems discussed above.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 2:
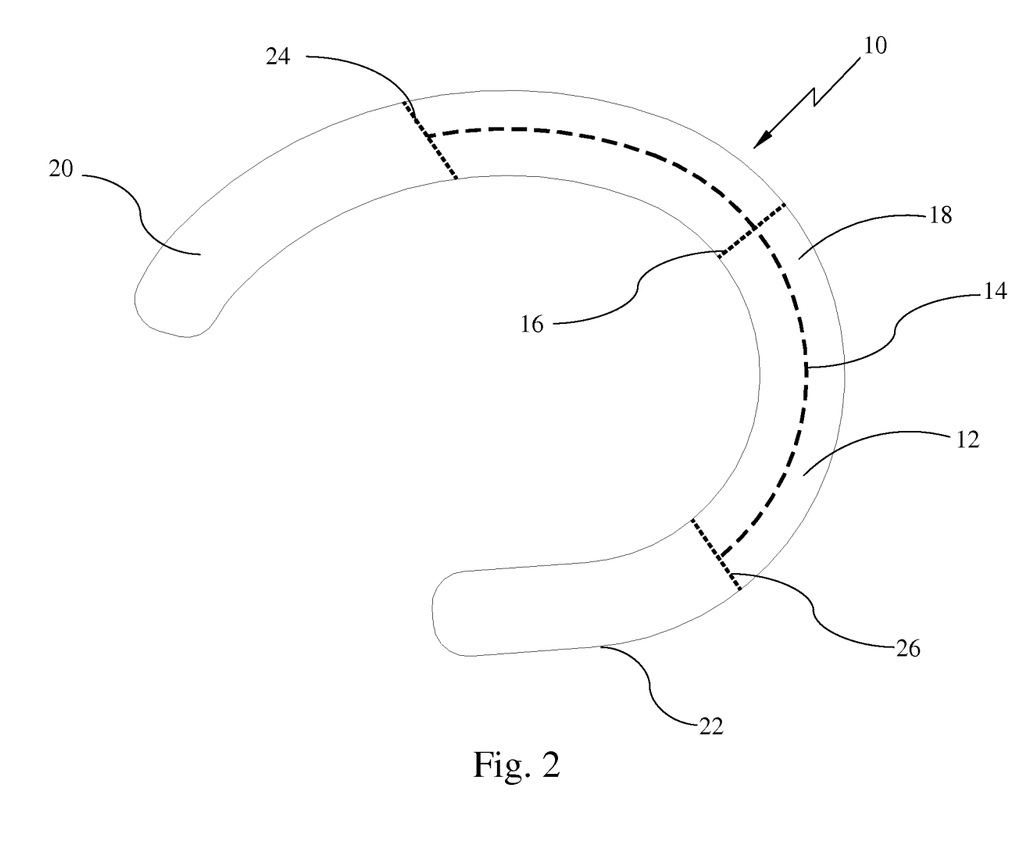
FIG. 2 is a plan view of an embodiment of a semi-flexible annuloplasty ring to treat functional tricuspid regurgitation.

A semi-flexible annuloplasty ring 10 is shown in a plan view in FIG. 2. As seen in FIG. 2, the semi-flexible annuloplasty ring 10 comprises an elongate tube of suturable material 12 formed into a C-shaped ring. In one specific embodiment described herein, the suturable material may be a biocompatible ribbon of heat settable material heat set into a tubular configuration as described in Wright, U.S. Pat. No. 5,674,279, the disclosure of which is hereby incorporated in its entirety herein. An example of a suitable heat settable material is Polyethertetraphylate (Polyester). Embodiments could also include other suitable braided, woven or knitted biocompatible materials such as Nylon or other biocompatible materials. The material must be suitable to readily receive a needle carrying a suture, a suture clip or other similar securing means and be capable of maintaining a position on an annulus of a heart valve without fraying once secured in place.

Figure 4:
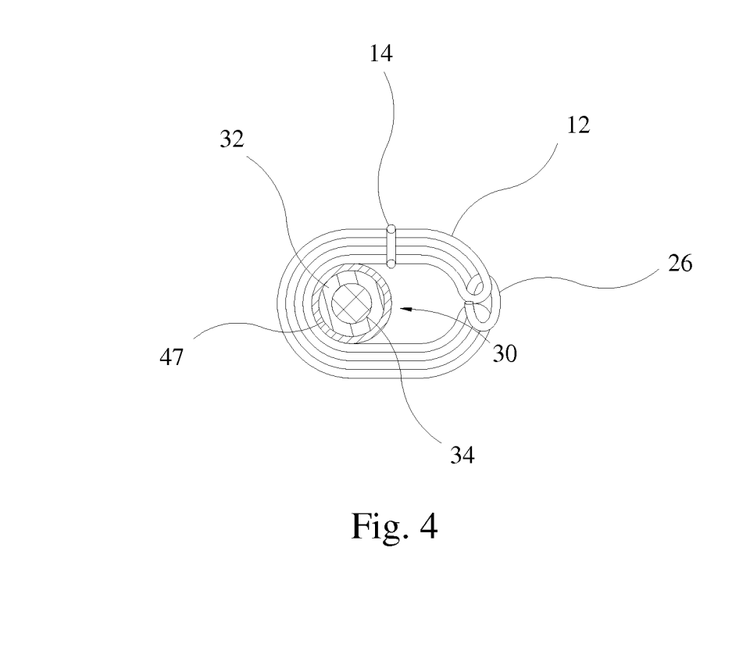
FIG. 4 is a cross-sectional view of the annuloplasty ring of FIG. 2 taken along line AA of FIG. 3.
Figure 5:
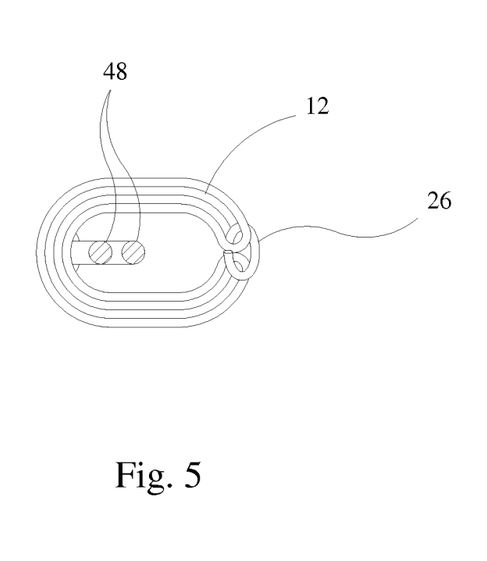
FIG. 5 is a cross-sectional view of the annuloplasty ring of FIG. 2 taken along line BB of FIG. 3.

Wright '279 describes a process of making a braided ribbon of material that includes starting with a heat-settable, meltable fiber tubing and sliding the tubing over a mandrel and then rolling the tubing back to form a double-walled tube. The double walled tube is cut to a desired length with a heated blade that cuts by melting the fibers infusing the fibers together to form a fused end with inner and outer walls being joined at a fused joint. The double wide tube is then slipped over a V-shaped mandrel which may be made of a more high temperature resistant polymer or metal and clamped between forming tools configured to define a V-shaped opening the size and shape of a desired V-shaped band. The band is then heat set at a temperature sufficient to set the polymer of which the tubing is formed without fusing. For example, if the tube is of polyester, temperatures in a range of 100-110° C. may be suitable and a heating period may be about 10 minutes. The opening of the V can be sewn together using lengthwise sutures thus forming a 4-walled tube as depicted, for example in FIGS. 3-5.

Various markers may be provided on the suturable material to aid a surgeon during installation of the semi-flexible annuloplasty ring 10 onto a valve annulus. For example, the embodiment illustrated in FIG. 2 is intended for installation on a tricuspid valve annulus. In this embodiment, the markers include a demarcation marker 14 and an anterior/posterior ("A/P") commissure marker 16. The demarcation marker 14 provides a visual indication to a surgeon of where sutures or suture clips can be placed without the needle or clip used for implanting interfering with an interior stiffener or operation of the semi-flexible annuloplasty ring 10. The A/P commissure marker is configured to align with the A/P commissure of the tricuspid heart valve and aid the surgeon in correctly placing the semi-flexible annuloplasty ring 10 on the tricuspid valve annulus (see FIG. 9). In embodiments configured for use with other heart valves other markers may be provided. In addition, in such embodiments the semi-flexible annuloplasty ring 10 may have a more symmetric C-shaped footprint than the embodiment of a semi-flexible annuloplasty ring 10 depicted in FIG. 2.

The embodiment of the semi-flexible annuloplasty ring 10 in FIG. 2 comprises a central segment 18, a first end segment 20 (also known as an anterior end) and a second end segment 22 (also known as a septal end). The central segment 18 is defined between radial suture seams 24, 26, which are used to secure an arcuate stiffener lengthwise within the central segment 18 as will be discussed in greater detail below.

Figure 3:
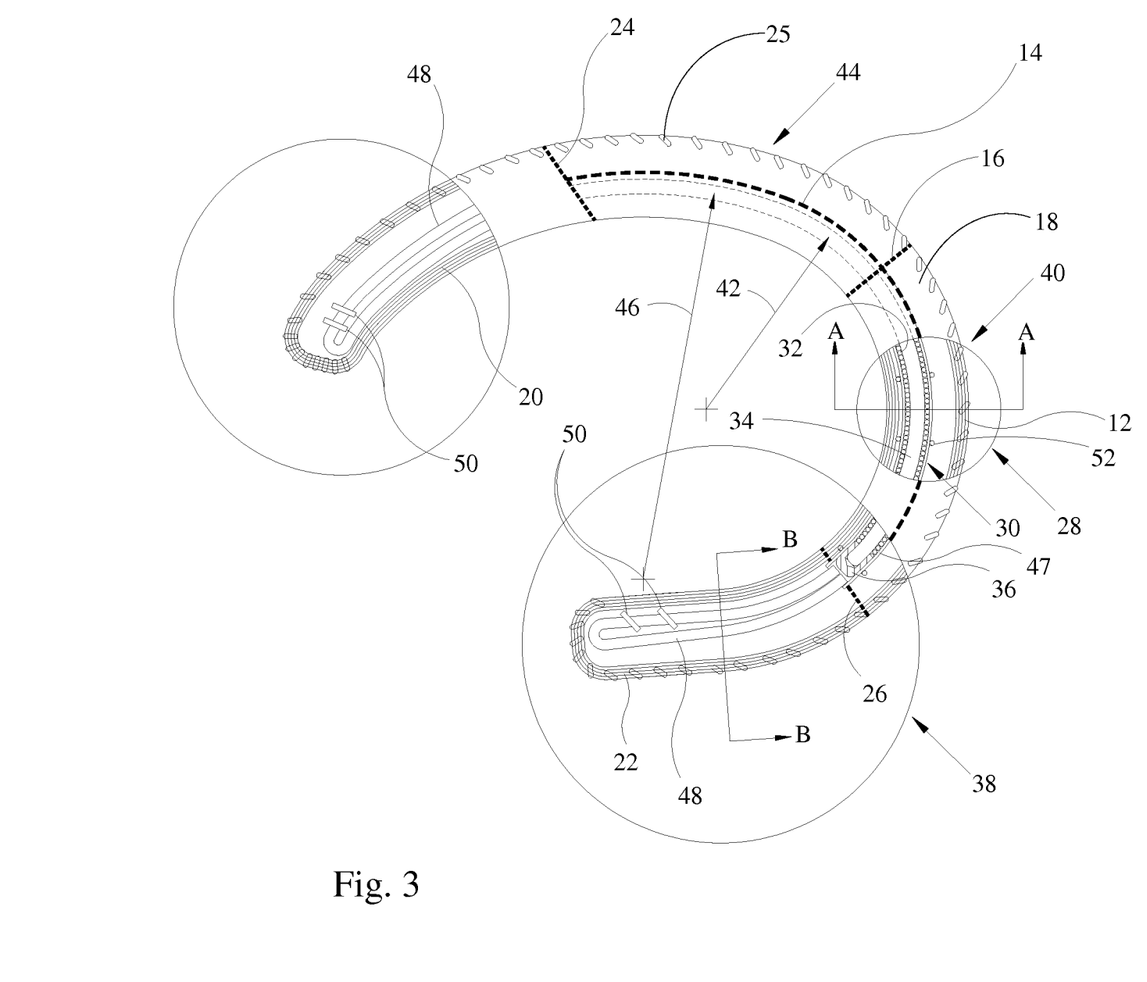
FIG. 3 is a partial sectional plan view of the annuloplasty ring of FIG. 2.

FIG. 3 depicts the semi-flexible annuloplasty ring 10 of FIG. 2 with various cutaway portions to illustrate the internal structure of the semi-flexible annuloplasty ring 10. Referring to the cutaway portion 28 in the central segment 18 (see also FIG. 4), the suturable material 12 is seen to comprise a number of layers as described in the Wright '279 patent referenced and described above. The suturable material 12 is formed into a tube by means of circumferential stitching forming a circumferential seam 25.

Within the central portion of the semi-flexible annuloplasty ring 10 resides an arcuate stiffener 30. The arcuate stiffener 30 in the illustrated embodiment comprises a close-coiled spring 32 of a biocompatible metal such as a Carpentier MP35N alloy. The spring may be wound using 0.009-0.012 inch diameter wire, although other wire diameters in the range of 0.005-0.020 inches are suitable. In the particular embodiment described herein, the spring has an inside diameter of about 0.029 inches and an outside diameter of about 0.055 inches. Other inside and outside diameters are within the scope of the invention. The helical coils of the spring define a spring cavity within the inside diameter. The stiffener 30 is configured to prevent lengthwise compression and to resist axial and radial deformation of the first circumferential segment. As used herein, "axial" and "radial" are relative to an axis of a valve annulus that extends in the direction of blood flow. Thus, "axial" deformation means in a direction along this axis and "radial" deformation means in a direction toward or away from the axis. "Axial and radial" deformation is intended to encompass only axial deformation, only radial deformation or deformation that is concurrently axial and radial. A stiffener wire 34 is axially received in the spring cavity to provide the resistance to axial and radial deformation. The stiffener wire 34 may be, for example, a biocompatible metal of the same composition as the spring to prevent galvanic corrosion. The stiffener wire should be of a diameter to resist radial deformation, as this phrase is defined above. By way of example, where the semi-flexible annuloplasty ring is to be used for a tricuspid valve to treat functional tricuspid regurgitation, a MP35N alloy, with a diameter of about 0.028 inches provides good results and a range of 0.015-0.050 inches (depending upon the desired stiffness and the ring size) generally being acceptable.

The stiffener wire 34 is secured lengthwise within the close coiled spring 32 by end caps 36 on each end of the stiffener. An end cap 36 proximate the second end segment 22 is shown in the cutaway portion 38 of FIG. 3. Although not shown, an identical end cap 36 is proximate the first end segment 20 abutting the radial suture seam 24. Each of the end caps 36 are radiused or chamfered to remove any sharp edge and may be hemispherical. The end caps are configured to prevent the stiffener from protruding through the suturable material 12 when the semi-flexible annuloplasty ring 10 is formed as illustrated in FIGS. 2 and 3. In the illustrated embodiment, the end caps have an outer diameter of about 0.046 inches. The stiffener 30 comprises a posterior portion 40 between the A/P commissure marker 16, and the radial suture seam 26 having a posterior radius 42 selected to conform the posterior portion 40 of the semi-flexible annuloplasty ring 10 to at least a posterior portion of a healthy tricuspid valve annulus prior to dilation (a "pre-dilated annulus"). The stiffener 30 further comprises an anterior portion 44 extending between the A/P commissure marker 16 and the radial suture seam 24. The anterior portion 44 has an anterior radius 46 that is larger than the posterior radius 42 and is selected so that with the semi-flexible annuloplasty ring 10 operatively attached to the annulus of a tricuspid valve, the anterior radius conforms to at least an anterior portion of the pre-dilated annulus. The close coiled spring 32 is received inside a silicon rubber tube 47.

The first end segment 20 and the second end segment 22 do not include a stiffener and as a result the first and second end segments are axially and radially deformable as will be described below. In the embodiment illustrated herein, an x-ray marker 48 is disposed within the tube and each of the first and second ends 20, 22. The x-ray marker 48 is non-structural in that it does not significantly inhibit radial or axial deformation of the first and second ends. In the illustrated embodiment, the x-ray marker 48 is a 0.020 inch silicone rubber band impregnated with tungsten and barium sulfate. Referring again to FIG. 3, the x-ray markers 48 are secured within the first and second end segments 20, 22 by feeding the x-ray marker 48 through braids 50 of the suturable material 12 that are teased out of the suturable material 12.

Figure 6:
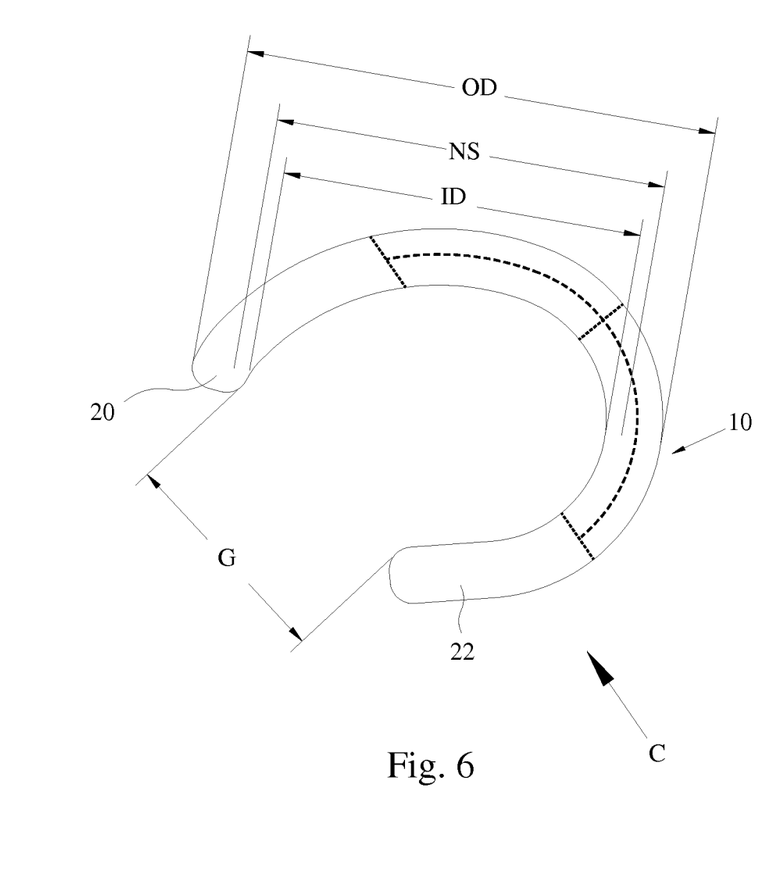
FIG. 6 is a plan view of the annuloplasty ring of FIG. 2 illustrating an outside diameter OD, inside diameter ID, nominal size NS and gap G between the anterior end and the septal end of the ring.
Figure 7:
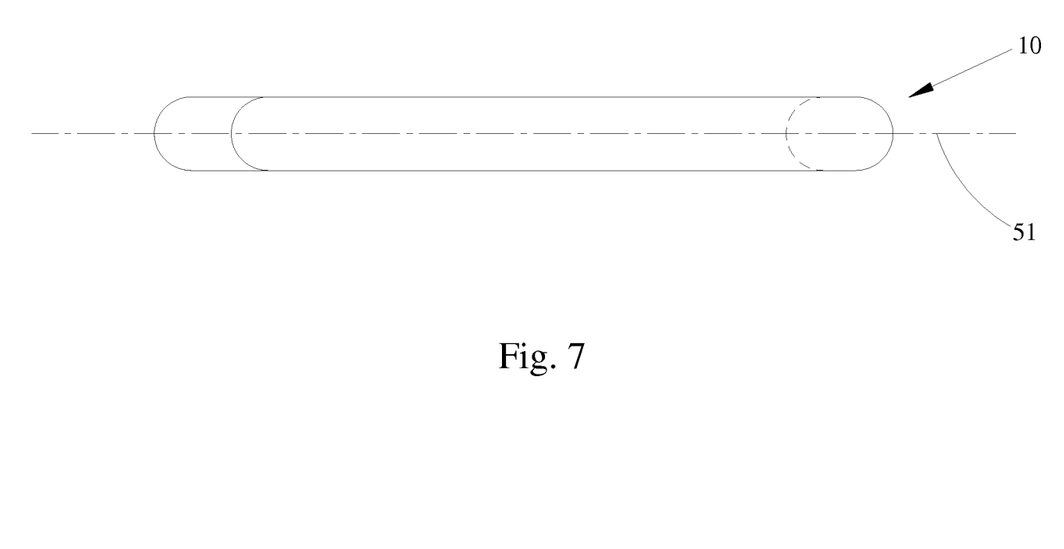
FIG. 7 is a side elevation of the annuloplasty ring of FIG. 2 taken in the direction of the arrow C of FIG. 6 showing the annuloplasty ring mounted on its holder (not shown)

The tube of suturable material 12 may be formed in a manner discussed in the Wright '279 patent referenced and described above. With the suturable material 12 formed into a length having a V-cross section, the stiffener 30 is placed at the bottom of the V and is held in place with tack stitches 52 (see FIG. 3) spaced circumferentially around the circumference of the stiffener 30. The x-ray markers 48 are likewise placed in bottom of the V and, as described above, are secured by feeding the x-ray marker 48 through the teased braids 50 of the suturable material 12. Thereafter the circumferential seam 25 is provided to form the V-cross section into a tube. The demarcation marker 14 and the A/P commissure marker 16 can be added as sutures. Further, the radial suture seams 24, 26 can be added to circumferentially confine the arcuate stiffener within the central segment. The assembled semi-flexible annuloplasty ring 10 is then preferably heat set to maintain the configuration as illustrated in FIGS. 2, 3 and 6-10. Referring to FIG. 6, the semi-flexible annuloplasty ring 10 is heat set to have a select outer diameter OD and a select inner diameter ID as illustrated. This leaves the semi-flexible annuloplasty ring 10 with a nominal size NS dimension as illustrated in FIG. 6. When heat set, the semi-flexible annuloplasty ring 10 further maintains a gap G between the first end segment 20 and second end segment 22. The gap G has a length greater than about 50% of a nominal size NS of the annuloplasty ring. In one embodiment, the gap G may have a length of about 60% of the nominal size NS. This size is selected to minimize the risk of damaging the atrioventricular (AV) node during implantation of the semi-flexible annuloplasty ring 10. Referring to FIG. 7, when heat set, the semi-flexible annuloplasty ring 10 is substantially planar about a plane 51 defined by the arcuate stiffener 30.

Figure 8:
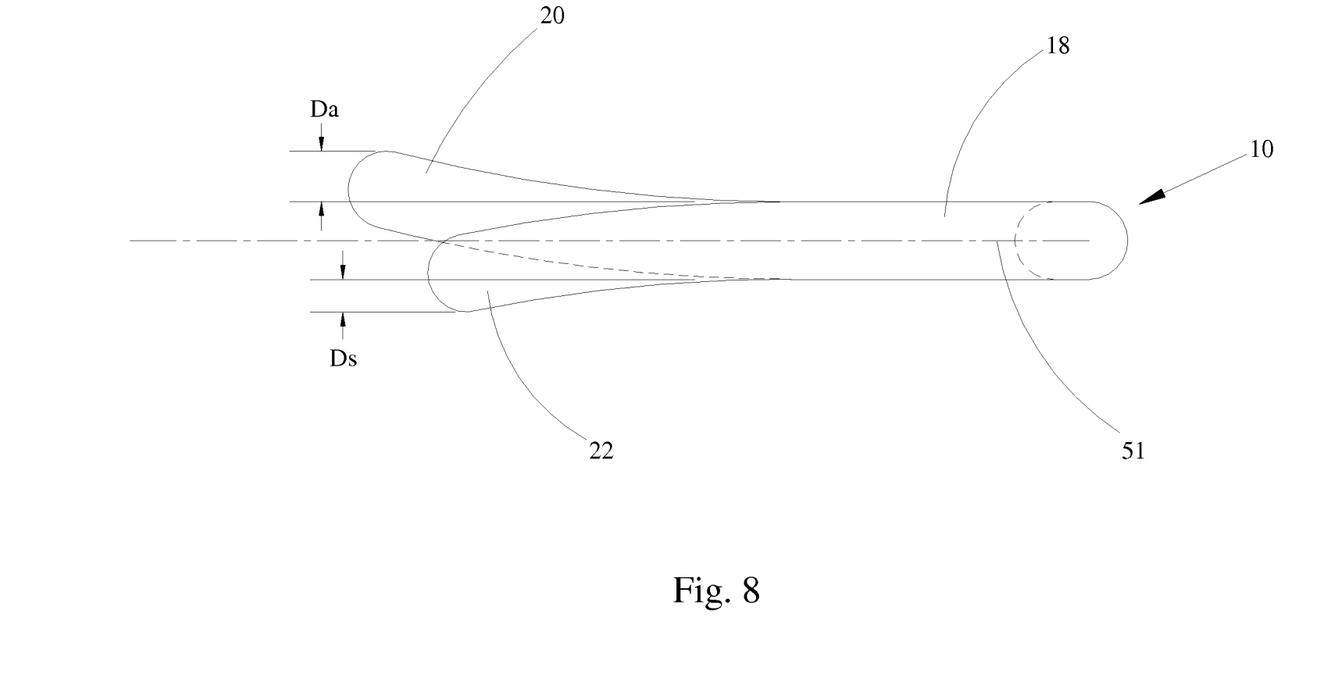
FIG. 8 is a side elevation of the annuloplasty ring of FIG. 2 taken in the direction of the arrow C of FIG. 6 showing the annuloplasty ring removed from a holder and axial displacement of the ring ends.

Referring to FIG. 8, the central segment 18 of the semi-flexible annuloplasty ring 10 is intended to remain substantially within the plane 51 of the arcuate stiffener 30. The first and second end segments 20, 22 are substantially free to deform axially in either direction as depicted in FIG. 8. Although not shown, the first and second end segments 20, 22 can also deform radially.

Figure 9:
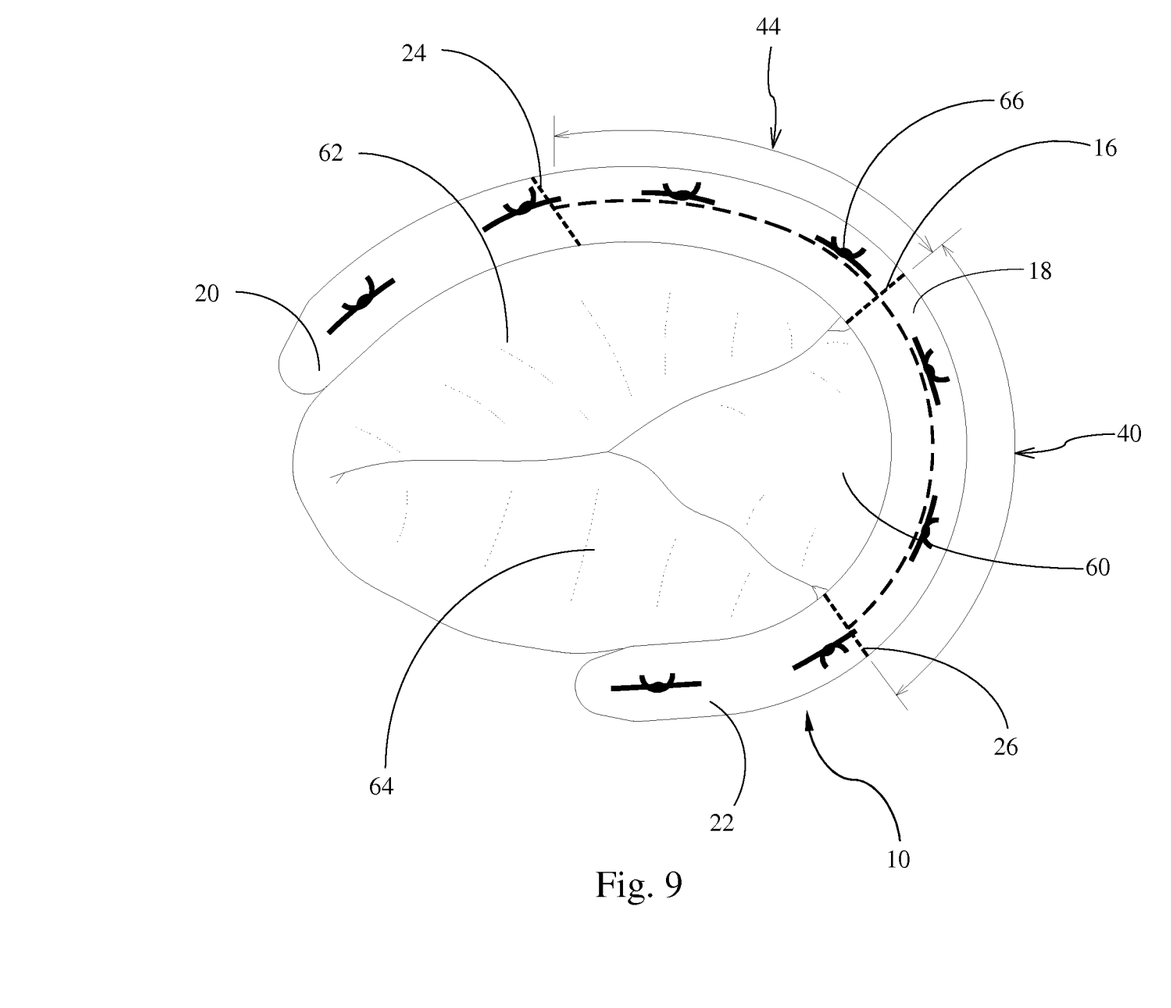
FIG. 9 is a schematic perspective view of the annuloplasty ring of FIG. 2 implanted on a corrected tricuspid valve annulus.

FIG. 9 illustrates the semi-flexible annuloplasty ring 10 operatively attached to a tricuspid valve of a heart with the right atrial wall cut and retracted to expose the tricuspid valve. The semi-flexible annuloplasty ring 10 is dimensioned and positioned to conform the tricuspid valve annulus to a pre-dilated or near-normal state. The posterior portion 40 is shown aligned with the tricuspid annulus at the base of the posterior leaflet 60. The anterior portion 44 of the central segment 18 overlies about one third the circumferential length of the anterior portion of the tricuspid valve annulus at the base of the anterior leaflet 62. The first end segment 20, which can also be referred to the anterior end, is secured to the anterior annulus as well. The second end segment 22, also known as the septal end, is attached to the septal portion of the tricuspid valve annulus at the base of the septal leaflet 64. As seen in FIG. 9, only 8 sutures 66 are required to secure the semi-flexible annuloplasty ring 10 to the tricuspid valve annulus. Depending on patient's anatomy, one or two or even three fewer or more sutures may be used. In any event, this is fewer than the 12-14 sutures required for implanting prior art annuloplasty rings to a tricuspid valve. Decreasing the number of sutures allows the semi-flexible annuloplasty ring 10 to be implanted more quickly, on the order of about fifteen minutes, which is considerably faster than prior art devices.

Figure 10:
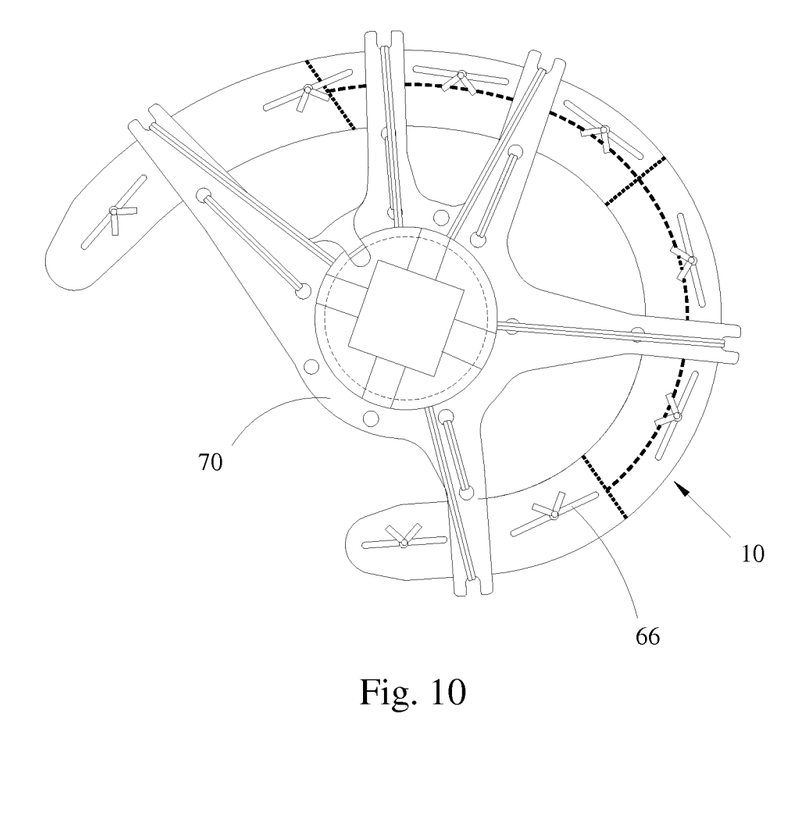
FIG. 10 is a plan view of a semi-flexible annuloplasty ring of FIG. 2 attached to a ring holder.

FIG. 10 is a plan view of a semi-flexible annuloplasty ring 10 of FIG. 2 attached to a holder 70. FIG. 10 further illustrates preferred locations of eight attachment sutures for implanting the annuloplasty ring on a tricuspid valve annulus.

The central portion 40 of the semi-flexible annuloplasty ring 10 maintains the attached portion of the tricuspid valve annulus substantially planar to prevent a "hammock" effect in the area of tricuspid annulus dilation. The flexible first and second end portions, on the other hand, can deform axially and radially to the tricuspid valve annulus to substantially eliminate stress on the attachment sutures and annulus tissue, while still controlling dilation of the tricuspid annulus and without substantially interfering with the normal function of the tricuspid valve. In other words, the flexible end portions do not inhibit the normal operative effectiveness of a tricuspid valve having a corrected or non-dilated annulus.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein and the Appendix are incorporated in their entirety by reference.

What is claimed is:

1. An annuloplasty ring configured for attachment to an annulus of a tricuspid valve, the tricuspid valve comprising an anterior leaflet, a posterior leaflet and a septal leaflet joined at an anterior/posterior commissure (A/P commissure), a posterior/septal commissure (P/S commissure) and a septal/anterior commissure (S/A commissure), respectively, the annuloplasty ring comprising:
    an elongate tube of suturable material terminating at opposing, first and second closed ends, the tube comprising a central segment and opposing, first and second end segments, each of the first and second end segments having an area of open space; wherein the first end segment extends from the first closed end to a first side of the central segment, and further wherein the second end segment extends from the second closed end to a second side of the central segment, the first side being opposite the second side;
    an arcuate stiffener received in the central segment of the tube and extending a length thereof, the arcuate stiffener being circumferentially confined within the central segment to prevent circumferential movement of the stiffener relative to the tube, the arcuate stiffener including an outer coil spring surrounding an internal stiffener wire;
    end caps on each end of the stiffener within the central segment, the end caps securing the internal stiffener wire lengthwise within the outer coil spring;
    at least one radial suture seam physically separating and positioned between each end cap and the adjacent area of open space; wherein each end cap abuts the at least one suture seam and
    the first and second end segments of the tube lacking a stiffener, whereby the first and second ends are axially deformable, the tube having a C-shaped configuration in a plane defined by the arcuate stiffener, the C-shaped configuration defining a diameter and a gap between the first and second closed ends, the gap having a length greater than 50% of the diameter.

2. The annuloplasty ring of claim 1 wherein the arcuate stiffener comprises a posterior portion having a posterior radius and an anterior portion having an anterior radius, the anterior radius being larger than the posterior radius.

3. The annuloplasty ring of claim 2 wherein the posterior radius and the anterior radius are selected so that with the annuloplasty ring operatively adapted for attachment to the annulus of a tricuspid valve, the posterior radius conforms to at least a posterior portion of the annulus in a pre-dilated state and the anterior radius conforms to a least a portion of an anterior portion of the annulus in a pre-dilated state.

4. The annuloplasty ring of claim 1 wherein the first and second ends are sufficiently axially deformable so that, when the annuloplasty ring is operatively configured for attachment to the annulus of a tricuspid valve, the first and second ends readily deviate from a plane defined by the arcuate stiffener to conform to the anatomy of tricuspid valve without interfering with its normal operation.

5. The annuloplasty ring of claim 1 wherein the elongate tube of suturable material comprises braided heat settable material heat set in a C-shaped configuration in a plane defined by the arcuate stiffener.

6. The annuloplasty ring of claim 1 wherein the arcuate stiffener is circumferentially confined within the central segment by a suture seam at each end of the arcuate stiffener; wherein each suture seam defines a boundary between the central segment and the adjacent end segment.

7. The annuloplasty ring of claim 1 further comprising an X-ray marker in each of the first and second end segments.

8. The annuloplasty ring of claim 7 wherein the X-ray marker is readily axially and radially deformable.

9. The annuloplasty ring of claim 1 wherein the first and second end segments are axially and radially deformable.

10. The annuloplasty ring of claim 1 further comprising about eleven or fewer attachment sutures spaced circumferentially.

11. An annuloplasty ring configured for attachment to an annulus of a tricuspid valve, the tricuspid valve comprising an anterior leaflet, a posterior leaflet and a septal leaflet joined at an anterior/posterior commissure (A/P commissure), a posterior/septal commissure (P/S commissure) and a septal/anterior commissure (S/A commissure), respectively, the annuloplasty ring comprising:
    an elongate tube of suturable material comprising a central segment and first and second end segments, each of the first and second end segments having an area of open space, wherein the first end segment extends from a first closed end to a first side of the central segment, and further wherein the second end segment extends from a second closed end to a second side of the central segment;
    an arcuate stiffener received in the central segment of the tube and extending a length thereof, the arcuate stiffener comprising an outer coil spring surrounding an internal stiffener wire, the arcuate stiffener being confined within the central segment to prevent circumferential movement of the stiffener relative to the tube, the arcuate stiffener further comprising a posterior portion having a posterior radius and an anterior portion having an anterior radius, the anterior radius being larger than the posterior radius, the tube having a C-shaped configuration in a plane defined by the arcuate stiffener, the C-shaped configuration defining a diameter and a gap between the first and second closed ends, the gap having a length greater than 50% of the diameter;
    end caps on each end of the stiffener wire within the central segment, the end caps securing the stiffener wire lengthwise within the outer coil spring; and
    one radial suture seam physically separating and positioned between each end cap and the adjacent area of open space, wherein each end cap abuts the suture seam.

12. The annuloplasty ring of claim 11 wherein the posterior radius and the anterior radius are selected so that with the annuloplasty ring operatively adapted for attachment to the annulus of a tricuspid valve, the posterior radius conforms to at least a posterior portion of the annulus in a pre-dilated state and the anterior radius conforms to a least a portion of an anterior portion of the annulus in a pre-dilated state.

13. The annuloplasty ring of claim 11 wherein the first and second ends are axially deformable so that, when the annuloplasty ring is operatively configured for attachment to the annulus of a tricuspid valve, the first and second ends readily deviate from a plane defined by the arcuate stiffener to conform to the anatomy of tricuspid valve without impairing tricuspid valve function.

14. The annuloplasty ring of claim 11 wherein the elongate tube of suturable material comprises braided heat settable material heat set in a C-shaped configuration in a plane defined by the arcuate stiffener.

15. The annuloplasty ring of claim 11 wherein the arcuate stiffener is secured to the suturable material by a suture seam at each end of the arcuate stiffener; wherein each suture seam defines a boundary between the central segment and the adjacent end segment.

16. The annuloplasty ring of claim 11 further comprising an X-ray marker in each of the first and second end segments.

* * * * *